(12) United States Patent
Hishikawa et al.

(10) Patent No.: US 9,434,794 B2
(45) Date of Patent: Sep. 6, 2016

(54) SILICON COMPOUND AND METHOD FOR PRODUCING SAME, AND USE THEREOF

(71) Applicant: TOYO TIRE & RUBBER CO., LTD., Osaka-shi, Osaka (JP)

(72) Inventors: Yasuhiro Hishikawa, Osaka (JP); Masaaki Kojima, Osaka (JP); Takashi Morinaga, Tsuruoka (JP); Takaya Sato, Tsuruoka (JP)

(73) Assignee: TOYO TIRE & RUBBER CO., LTD., Osaka (JP)

( * ) Notice: Subject to any disclaimer, the term of this patent is extended or adjusted under 35 U.S.C. 154(b) by 0 days.

(21) Appl. No.: 14/384,012

(22) PCT Filed: Mar. 28, 2013

(86) PCT No.: PCT/JP2013/002136
§ 371 (c)(1),
(2) Date: Sep. 9, 2014

(87) PCT Pub. No.: WO2013/150751
PCT Pub. Date: Oct. 10, 2013

(65) Prior Publication Data
US 2015/0038643 A1    Feb. 5, 2015

(30) Foreign Application Priority Data

Apr. 2, 2012  (JP) ................. 2012-084289
Apr. 2, 2012  (JP) ................. 2012-084290

(51) Int. Cl.
| | | |
|---|---|---|
| C08F 4/72 | (2006.01) | |
| C08F 292/00 | (2006.01) | |
| C08L 51/10 | (2006.01) | |
| C07F 7/18 | (2006.01) | |
| C08K 9/06 | (2006.01) | |
| C08L 9/06 | (2006.01) | |
| C08F 2/38 | (2006.01) | |
| C08F 4/00 | (2006.01) | |
| C08F 4/58 | (2006.01) | |
| C08L 51/04 | (2006.01) | |
| C08F 220/18 | (2006.01) | |

(52) U.S. Cl.
CPC ............... *C08F 4/72* (2013.01); *C07F 7/1836* (2013.01); *C07F 7/1892* (2013.01); *C08F 2/38* (2013.01); *C08F 4/00* (2013.01); *C08F 4/58* (2013.01); *C08F 292/00* (2013.01); *C08K 9/06* (2013.01); *C08L 9/06* (2013.01); *C08L 51/04* (2013.01); *C08L 51/10* (2013.01); *C08F 2220/185* (2013.01); *C08F 2438/01* (2013.01)

(58) Field of Classification Search
CPC ............ C08F 2/38; C08F 4/58; C08L 51/04; C07F 7/1836; C08K 9/06
See application file for complete search history.

(56) References Cited

U.S. PATENT DOCUMENTS

| | | | | |
|---|---|---|---|---|
| 7,294,731 B1* | 11/2007 | Flynn | ................... | C07F 7/1836 556/427 |
| 8,741,994 B1* | 6/2014 | Hishikawa | ................... | 524/188 |
| 2008/0050600 A1 | 2/2008 | Fan et al. | | |
| 2010/0222504 A1* | 9/2010 | Minge et al. | .................. | 524/588 |
| 2010/0298446 A1* | 11/2010 | Chang et al. | ............... | 514/772.4 |
| 2015/0038643 A1* | 2/2015 | Hishikawa et al. | ........... | 524/783 |

FOREIGN PATENT DOCUMENTS

| | | |
|---|---|---|
| JP | 04-112893 A | 4/1992 |
| JP | 08-104710 A | 4/1996 |
| JP | 2510345 B2 | 6/1996 |
| JP | 2006-113389 A | 4/2006 |
| JP | 2006-213661 A | 8/2006 |
| JP | 2006-273588 A | 10/2006 |
| JP | 2007-8859 A | 1/2007 |
| JP | 2009-299044 A | 12/2009 |
| WO | 2005/108451 A1 | 11/2005 |
| WO | 2008/130872 A2 | 10/2008 |
| WO | 2010/135481 A1 | 11/2010 |

OTHER PUBLICATIONS

International Search Report dated Jul. 2, 2013, issued in corresponding application No. PCT/JP2013/002136.
Ohno et al., "Synthesis of Monodisperse Silica Particles Coated with Well-Defined, High-Density Polymer Brushes by Surface-Initiated Atom Transfer Radical Polymerization", Macromolecules, Feb. 9, 2005, pp. 2137-2142, vol. 38.
Rotzoll et al., "Controlled Radical Polimerization Trithiocarbonates Containing Trimethoxysilyl Functionalities as Mediating Agents in Reversible Addition-Fragmentation Chain Transfer (RAFT) Polymerization of Methyl Acrylate", Macromolecular Symposia, 2009, pp. 1-12, vol. 275-276, No. 1.
Li et al., "Synthesis of Shape Amphiphiles Based on POSS Tethered with Two Symmetric/Asymmetric Polymer Tails via Sequential "Grafting-from" and Thiol-Ene "Click" Chemistry", ACS Macro Letters, Jun. 19, 2012, pp. 834-839, vol. 1, No. 7.
German Office Action dated Dec. 3, 2014, issued in corresponding DE Application No. 11 2013 001 523.4 with English translation (10 pages).
Office Action dated Nov. 4, 2015, issued in counterpart Chinese Application No. 201380018898.9, with English translation. (12 pages).
Office Action dated Dec. 1, 2015, issued in counterpart Japanese Application No. 2012-084289, with English translation. (10 pages).

* cited by examiner

*Primary Examiner* — Michael A Salvitti
(74) *Attorney, Agent, or Firm* — Westerman, Hattori, Daniels & Adrian, LLP

(57) ABSTRACT

A novel silicon compound capable of initiating radical polymerization is provided. The silicon compound is represented by the following general formula (1)

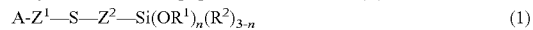

$$A-Z^1-S-Z^2-Si(OR^1)_n(R^2)_{3-n} \quad (1)$$

wherein A is a group capable of initiating radical polymerization, $Z^1$ and $Z^2$ are each independently a bivalent group that has at least a carbon atom, $R^1$ and $R^2$ are each independently an alkyl group having from 1 to 3 carbon atoms, and n is an integer of 1 to 3. A radical polymerization initiator comprising the silicon compound, and a polymer obtained by radical polymerization of a monomer with the radical polymerization initiator are also provided. Also provided is a complex having a polymer graft chain formed on a solid substance surface with the use of the silicon compound.

21 Claims, No Drawings

SILICON COMPOUND AND METHOD FOR PRODUCING SAME, AND USE THEREOF

TECHNICAL FIELD

The present invention relates to novel silicon compounds, and a method for producing same. The present invention also relates to a radical polymerization initiator comprising the silicon compounds, a method for producing a polymer using same, and rubber compositions containing the polymer. The present invention also relates to a complex of a solid substance with a polymer graft chain formed by using the silicon compound, a method for producing same, and molded articles comprising the complex. The present invention also relates to a reinforcing agent contained in rubber compositions and plastic compositions, a method for producing same, and rubber compositions and plastic compositions containing the reinforcing agent.

BACKGROUND ART

For grafting of a polymer on a surface of a solid substance, there have been attempts to produce a thick polymer brush on a solid substance surface through living radical polymerization. In this method, a polymerization initiator is immobilized on a particle surface of a solid substance beforehand, and then various monomers are polymerized to form a polymer graft chain.

For example, Patent Literature 1 and Non-Patent Literature 1 disclose using polymerization initiators that can be used for a silane coupling process against a solid substance surface. Specifically, these publications disclose a polymerization initiator (2-bromo-2-methyl)propionyloxyhexyltriethoxysilane (BHE). BHE is synthesized by hydrosilylation reaction of alkoxysilane with the double bond formed at one end of a compound having a radical polymerization initiation group at the other end of the molecular chain. However, it cannot be said that this producing method is industrially useful because the hydrosilylation reaction has only moderate reaction efficiency.

Patent Literatures 2 and 3 disclose methods of producing a silicon compound capable of initiating living radical polymerization. The methods include a hydrosilylation reaction of chlorosilane, followed by a reaction with orthoformate or alcohol to introduce an alkoxy group. The methods can improve reaction efficiency, but are problematic in that the catalysts of the hydrosilylation reaction are water prohibitive.

Rubber compositions and plastic compositions conventionally contain a reinforcing agent (or reinforcing filler as it is also called). For example, silica is contained as a reinforcing agent as a means to meet the demand for the development of a low-heat-generating rubber composition in tire applications where high fuel efficiency is required. However, silica has poor interaction with the matrix diene rubber because of the high polarity of the silica particle surface. Patent Literature 4 attempts to improve silica dispersibility with a method in which silica is coated with polymer through radical polymerization after being impregnated with a vinyl monomer.

CITATION LIST

Patent Literature

PTL 1: WO2005/108451
PTL 2: JP-A-2006-213661
PTL 3: JP-A-2007-008859
PTL 4: JP-A-2006-273588

Non Patent Literature

NPL 1: Kohji Ohno et al., *Synthesis of Monodisperse Silica Particles Coated with Well-Defined, High-Density Polymer Brushes by Surface-Initiated Atom Transfer Radical Polymerization*, Macromolecules, Vol. 38, No. 6, p. 2137-2142, 2005

SUMMARY OF INVENTION

Technical Problem

An object of the present invention is to provide novel silicon compounds capable of initialing radical polymerization, a method for producing same, and various uses thereof.

Solution to Problem

A silicon compound according to First Embodiment is represented by the following general formula (1).

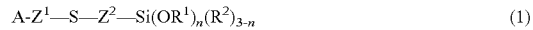

In the formula (1), A is a group capable of initiating radical polymerization, $Z^1$ and $Z^2$ are each independently a bivalent group that has at least a carbon atom, $R^1$ and $R^2$ are each independently an alkyl group having from 1 to 3 carbon atoms, and n is an integer of 1 to 3.

According to Second Embodiment, there is provided a method for producing a silicon compound represented by the following general formula (5), the method comprising reacting the compound of the following general formula (6) with the compound of the following general formula (7).

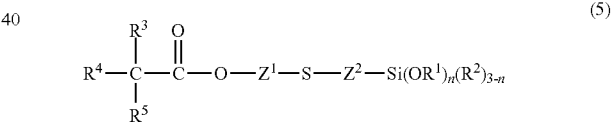

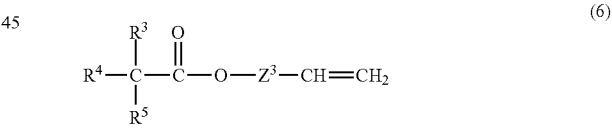

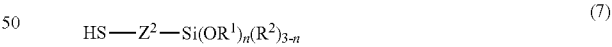

In the formulae, $R^1$ and $R^2$ are each independently an alkyl group of 1 to 3 carbon atoms, $R^3$, $R^4$, and $R^5$ are each independently a structure configured from at least one selected from the group consisting of carbon, hydrogen, oxygen, nitrogen, halogen, and sulfur, and at least one of $R^3$, $R^4$, and $R^5$ is halogen, and wherein $Z^1$, $Z^2$, and $Z^3$ are each independently a bivalent group that has at least a carbon atom, and n is an integer of 1 to 3.

According to Third Embodiment, there is provided a radical polymerization initiator that comprises the silicon compound of First Embodiment.

According to Fourth Embodiment, there is provided a polymer producing method of subjecting a monomer to radical polymerization or living radical polymerization with the radical polymerization initiator of Third Embodiment.

According to Fifth Embodiment, there is provided a polymer having a terminal alkoxysilyl group and obtained by using the method of Fourth Embodiment.

According to Sixth Embodiment, there is provided a rubber composition that contains the polymer of Fifth Embodiment in 0.1 to 100 parts by mass with respect to 100 parts by mass of a rubber component.

According to Seventh Embodiment, there is provided a complex producing method that comprises fixing the silicon compound of First Embodiment to a solid substance surface, and polymerizing a monomer from the fixed silicon compound through living radical polymerization to form a polymer graft chain.

According to Eighth Embodiment, there is provided a complex obtained by using the method of Seventh Embodiment.

According to Ninth Embodiment, there is provided a molded article comprising the complex of Eighth Embodiment.

According to Tenth Embodiment, there is provided a method for producing a rubber or plastic reinforcing agent, the method comprising fixing the silicon compound of First Embodiment to a solid substance surface, and polymerizing a radically polymerizable monomer through living radical polymerization started from the fixed silicon compound at the group capable of initiating radical polymerization.

According to Eleventh Embodiment, there is provided a rubber or plastic reinforcing agent, wherein the reinforcing agent is obtained by using the producing method of Tenth Embodiment, and wherein the amount of the polymer graft chain on the solid substance surface is 5 to 1,000 parts by mass with respect to 100 parts by mass of the solid substance.

According to Twelfth Embodiment, there is provided a rubber composition that contains the reinforcing agent of Eleventh Embodiment in 1 to 200 parts by mass with respect to 100 parts by mass of a rubber component.

According to Thirteenth Embodiment, there is provided a plastic composition that contains the reinforcing agent of Eleventh Embodiment in 1 to 200 parts by mass with respect to 100 parts by mass of a plastic component.

Advantageous Effects of Invention

According to the present embodiment, novel silicon compounds capable of initiating radical polymerization are provided. The silicon compounds are preferred for use as radical polymerization initiators, and have use, for example, as polymerization initiators that are immobilizable on various materials. The present invention also enables production of the silicon compounds with a simple method.

DESCRIPTION OF EMBODIMENTS

Silicon Compounds

A silicon compound according to the present embodiment is represented by the general formula (1) above. The silicon compound has unpaired electrons on the sulfur atom of the thioether group present in the structure. The silicon compound thus has high affinity to metals, inorganic substances, and polymer materials. This is believed to improve fixability for a solid substance surface, and dispersibility for matrixes such as polymers and rubbers as compared to when a thioether group is not present.

In the formula (1), A is a group capable of initiating radical polymerization (hereinafter, also referred to simply as "radical polymerization initiation group"). Preferably, A is a group capable of initiating living radical polymerization (i.e., living radical polymerization initiation group). The form of living radical polymerization reaction is not particularly limited, and may be, for example, atom transfer radical polymerization (ATRP), reversible addition-fragmentation chain transfer polymerization (RAFT), a method based on iniferter, or reversible chain transfer catalyzed polymerization (RTCP).

Examples of the group capable of initiating atom transfer radical polymerization include a haloalkyl group, a haloester group, a haloalkylphenyl group, a haloketone group, a halonitrile group, a halogenated sulfonyl group, and a dithiocarbamate group. Preferred are a haloester group, and a haloalkylphenyl group. In this case, polymerization reaction proceeds with radicals generated in the presence of a transition metal complex such as a copper chloride/amine complex. Examples of the group capable of initiating reversible addition-fragmentation chain transfer polymerization include a dithioester group, a trithiocarbonate group, a xanthate group, and a dithiocarbomate group. In this case, an azo compound or an organic peroxide is used as a polymerization catalyst. Examples in the case of the iniferter include a dithiocarbamate group. Examples in the case of the reversible chain transfer catalyzed polymerization include an alkyl iodide group. In this case, polymerization reaction proceeds with radicals generated in the presence of a radical generating agent and an iodide catalyst.

Examples of the haloalkyl group include trichloromethyl, and bromodichloromethyl. Examples of the haloalkylphenyl group include chloromethyl phenyl, bromomethyl phenyl, iodomethyl phenyl, (1-chloroethyl)phenyl, (1-bromoethyl)phenyl, and (1-iodoethyl)phenyl. Examples of the haloketone group include trichloro ethanoyl, and dichloro ethanoyl. Examples of the halonitrile group include chlorocyanomethyl, bromocyanomethyl, and iodocyanomethyl. Examples of the halogenated sulfonyl group include chlorosulfonyl.

Preferred as the radical polymerization initiation group represented by A is the α-haloester group represented by the following general formula (2).

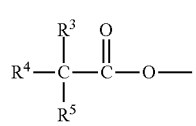

(2)

In the formula (2), $R^3$, $R^4$, and $R^5$ are each independently a structure configured from at least one selected from the group consisting of a carbon atom, a hydrogen atom, an oxygen atom, a nitrogen atom, a halogen atom, and a sulfur atom, and at least one of $R^3$, $R^4$, and $R^5$ is a halogen atom. The halogen is preferably chlorine, bromine, or iodine, more preferably bromine $R^3$, $R^4$, and $R^5$ are each basically a hydrogen atom, a hydrocarbon group, or a halogen atom, and may include a substituent that contains at least one heteroatom selected from the group consisting of oxygen, nitrogen, and sulfur, provided that the radical polymerization initiating capability remains intact. In an embodiment, $R^3$ is a halogen atom, and $R^4$ and $R^5$ are each independently a hydrogen atom, an alkyl group having from 1 to 20 carbon atoms, an aryl group having from 6 to 20 carbon atoms, or an arylalkyl group having from 7 to 20 carbon atoms, wherein $R^4$ and $R^5$ are not hydrogen at the same time. The alkyl group is preferably an alkyl group having from 1 to 4 carbon atoms. The aryl group is preferably a phenyl group, or a methylphenyl group. The arylalkyl group is preferably a benzyl group, or a phenethyl group. Particularly preferred as $R^4$ and $R^5$ are, for example, methyl groups.

Also preferred as the radical polymerization initiation group represented by A is the thiocarbonylthio group represented by the following general formula (3).

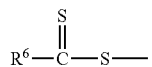
(3)

In the formula (3), $R^6$ is a structure configured from at least one selected from the group consisting of a carbon atom, a hydrogen atom, an oxygen atom, a nitrogen atom, a halogen atom, and a sulfur atom. The thiocarbonylthio group is a dithioester group when $R^6$ is a hydrocarbon group. The thiocarbonylthio group is a trithiocarbonate group when $R^6$ is $R^9$—S— (where $R^9$ is hydrocarbon). The thiocarbonylthio group is a xanthate group when $R^6$ is $R^{10}$—O— (where $R^{10}$ is hydrocarbon). The thiocarbonylthio group is a dithiocarbamate group when $R^6$ is $R^{11}R^{11}R^{12}N$— (where $R^{11}$ and $R^{12}$ are each independently a hydrogen atom or a hydrocarbon group). These thiocarbonylthio groups may have a substituent that contains at least one heteroatom selected from the group consisting of oxygen, nitrogen, and halogen, provided that the radical polymerization initiating capability remains intact. In the case of a dithioester group, $R^6$ is preferably an alkyl group having from 1 to 20 carbon atoms, an aryl group having from 6 to 20 carbon atoms, or an arylalkyl group having from 7 to 20 carbon atoms, particularly preferably a phenyl group. In the case of a trithiocarbonate group and a xanthate group, $R^9$ and $R^{10}$ are each preferably an alkyl group having from 1 to 20 carbon atoms, an aryl group having from 6 to 20 carbon atoms, or an arylalkyl group having from 7 to 20 carbon atoms, particularly preferably an alkyl group having from 1 to 12 carbon atoms. In the case of a dithiocarbamate group, $R^{11}$ and $R^{12}$ are each independently a hydrogen, an alkyl group having from 1 to 12 carbon atoms, or an aryl group having from 6 to 10 carbon atoms. More preferably, $R^{11}$ is an alkyl group, and $R^{12}$ is an aryl group. $R^{11}$ and $R^{12}$ may be bonded to each other to form a ring with N.

In the formula (1), $Z^1$ is a bivalent group that binds the radical polymerization initiation group represented by A and the thioether group represented by —S—. In an embodiment, $Z^1$ is a bivalent organic group having from 1 to 20 carbon atoms. The organic group may include an ether bond, and may have a substituent that contains at least one heteroatom selected from the group consisting of oxygen, nitrogen, halogen, and sulfur. More preferably, $Z^1$ is an alkylene group having from 3 to 11 carbon atoms.

In the formula (1), $Z^2$ is a bivalent group that binds the thioether group and the alkoxysilyl group represented by —Si(OR$^1$)$_n$(R$^2$)$_{3-n}$. In an embodiment, $Z^2$ is a bivalent organic group having from 1 to 20 carbon atoms. The organic group may include an ether bond, and may have a substituent that contains at least one heteroatom selected from the group consisting of oxygen, nitrogen, halogen, and sulfur. More preferably, $Z^2$ is an alkylene group having from 1 to 3 carbon atoms.

In the formula (1), $R^1$ is an alkyl group having from 1 to 3 carbon atoms, preferably, a methyl group or an ethyl group. When more than one $R^1$ exists within the molecule, the plurality of $R^1$ may be the same or different. $R^2$ is an alkyl group having from 1 to 3 carbon atoms, preferably a methyl group or an ethyl group. When more than one $R^2$ exists within the molecule, the plurality of $R^2$ may be the same or different. n is an integer of 1 to 3, and preferably n=3. Specifically, the alkoxysilyl group represented by —Si(OR$^1$)$_n$(R$^2$)$_{3-n}$ is preferably a trialkoxysilyl group, more preferably a triethoxysilyl group or a trimethoxysilyl group.

In a certain embodiment, the silicon compound may be the silicon compound represented by the following general formula (4).

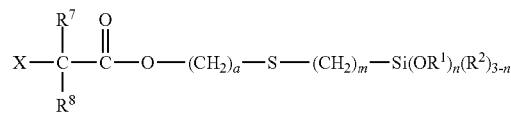
(4)

In the formula (4), X is a halogen atom, preferably chlorine, bromine, or iodine, more preferably bromine $R^1$ and $R^2$ are each independently an alkyl group having from 1 to 3 carbon atoms, preferably a methyl group or an ethyl group. $R^7$ and $R^8$ are each independently a hydrogen atom, or an alkyl group having from 1 to 3 carbon atoms, and are not hydrogen atoms at the same time. $R^7$ and $R^8$ are each preferably a methyl group or an ethyl group, further preferably a methyl group. a is an integer of 3 to 11, and m is an integer of 1 to 3. n is an integer of 1 to 3, and preferably n=3.

The silicon compound of the formula (4) has an α-haloester group as the radical polymerization initiation group. This is when A, $Z^1$, and $Z^2$ in the formula (1) are represented by the following formulae (4-1), (4-2), and (4-3), respectively. In these formulae, X, $R^7$, $R^8$, a, and m are the same as in the formula (4).

(4-1)

(4-2)

(4-3)

Silicon Compound Producing Method

The silicon compounds of the foregoing embodiments may be synthesized by reaction of a compound having a radical polymerization initiation group and a carbon-carbon double bond within the molecule, and a silane coupling agent having a mercapto group. Specifically, the silicon compound represented by the general formula (5) below may be produced by reaction of a compound of the general formula (6) with a compound of the general formula (7). The silicon compound represented by the formula (5) has the α-haloester group of the general formula (2) as the radical polymerization initiation group of the general formula (1). The detailed descriptions of the producing method below are based on this silicon compound. It should be noted, however, that the producing method also may be performed in the same manner when the radical polymerization initiation group contained is the thiocarbonylthio group represented by the general formula (3), or some other radical polymerization initiation group.

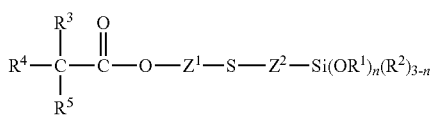

(5)

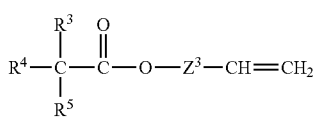

(6)

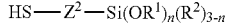

(7)

In the formulae (5) to (7), $R^1$, $R^2$, $Z^1$, $Z^2$, and n are the same as in the formula (1). $R^3$, $R^4$, and $R^5$ are the same as in the formula (2). $Z^3$ is a bivalent group that has a carbon atom. In an embodiment, $Z^3$ is a bivalent organic group having from 1 to 18 carbon atoms. The organic group may include an ether bond, and may have a substituent that contains at least one heteroatom selected from the group consisting of oxygen, nitrogen, halogen, and sulfur. More preferably, $Z^3$ is an alkylene group having from 1 to 9 carbon atoms, or a group with two fewer carbon atoms than in $Z^1$.

The compound represented by the formula (6) is the compound that has a radical polymerization initiation group and a double bond within the molecule. The compound represented by the formula (7) is the silane coupling agent having a mercapto group. In this reaction, the mercapto group in the compound of the formula (7) is bonded to the double bond in the compound of the formula (6) through ene-thiol reaction.

A radical generating agent is used as the reaction catalyst in the reaction. Examples of the radical generating agent include azo compounds, and organic peroxides, including compounds that produce radicals under heat or light. Examples of the azo compounds include azobisisobutyronitrile (AIBN), and 1,1'-azobis(cyclohexanecarbonitrile) (ABCN). Examples of the organic peroxides include di-tert-butyl peroxide, tert-butyl hydroperoxide, benzoyl peroxide, and methyl ethyl ketone peroxide. Contrary to the general expectation that the compound of the formula (6) would undergo polymerization with its vinyl bond when such a radical generating agent is used, what was actually observed was that the ene-thiol reaction preferentially proceeded, and produced the silicon compound of the formula (5).

Specifically, the reaction may be performed by mixing the compound of the formula (6), the compound of the formula (7), and a radical generating agent with an organic solvent such as toluene, and maintaining the mixture under conditions that generate radicals. The reaction temperature is not particularly limited, and is preferably 50 to 120° C.

The method used to synthesize the compound of the formula (6) is not particularly limited, and the methods disclosed in Patent Literatures 2 and 3 may be used for synthesis. Specifically, for example, methods may be used in which an acid halide with the halogen atom attached to the α carbon is reacted in the presence of triethylamine with a compound having a hydroxyl group at one end, and an addition polymerizable double bond at the other end of the molecular chain. The compound of the formula (7) is not particularly limited, and may be a commercially available silane coupling agent having a mercapto group. Alternatively, the compound of the formula (7) may be synthesized by using a known method.

In the present embodiment, a preferred form of the silicon compound represented by the formula (4) may be produced by reacting compounds of the following general formulae (8) and (9).

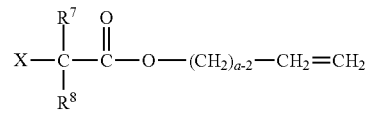

(8)

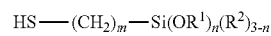

(9)

In the formulae (8) and (9), X, $R^1$, $R^2$, $R^7$, $R^8$, a, m, and n are the same as in the formula (4).

Radical Polymerization Initiator, Modified Polymer Using Same, and Method of Production Thereof The silicon compound according to the present embodiment has a radical polymerization initiation group within the molecule, and can be used as a radical polymerization initiator, more preferably a living radical polymerization initiator. Specifically, a radical polymerization initiator comprising the silicon compound may be used to produce a polymer through radical polymerization or living radical polymerization of at least one monomer selected from the group consisting of a vinyl monomer and a diene monomer.

The product polymer has the alkoxysilyl group of silicon compound origin at an end of the polymer molecule, and can be regarded as a modified polymer. The alkoxysilyl group can react with an inorganic substance such as silica, and can improve the affinity of the polymer to inorganic substance. In an embodiment, the modified polymer has a polymer chain (preferably, a vinyl polymer chain) formed by living radical polymerization of the monomer, and a structure of the following formula (1-1) at one end of the polymer chain.

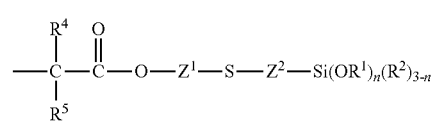

(1-1)

In the formula (1-1), $R^1$, $R^2$, $Z^1$, $Z^2$, and n are the same as in the formula (1). $R^4$ and $R^5$ are the same as in the formula (2). The structure represented by the formula (1-1) may be obtained by polymerization with an initiator of the formula (2) capable of initiating ATRP living radical polymerization ($R^3$ is halogen). The product modified polymer has the structure of the formula (1-1) at one end, and halogen ($R^3$) at the other end of the molecular chain. More preferably, an initiator represented by the formula (4) is used to polymerize and obtain a modified polymer that has the structure of the formula (4-4) below at one end of the polymer chain. In this case, the product modified polymer has a halogen (X) at the other end. In the formula (4-4), $R^1$, $R^2$, $R^7$, $R^8$, a, m, and n are the same as in the formula (4).

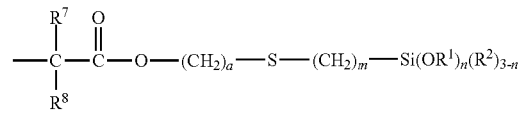

(4-4)

The vinyl monomer may be, for example, at least one selected from the group consisting of (meth)acrylic acid monomer, (meth)acrylamide monomer, styrene monomer, vinyl ester monomer, nitrile vinyl monomer, vinyl ether monomer, and monoolefin monomer. As used herein, "(meth)acrylic acid" means acrylic acid and/or methacrylic acid, and "(meth)acrylamide" means acrylamide and/or methacrylamide.

Examples of the (meth)acrylic acid monomer include (meth)acrylic acids, and derivatives thereof, including, for example, acrylic acid, methyl acrylate, ethyl acrylate, 2-carboxyethyl acrylate, 2-(dimethylamino)ethyl acrylate, 1,1,1,3,3,3-hexafluoroisopropyl acrylate, butyl acrylate, sodium acrylate, isobornyl acrylate, propargyl acrylate, ethylene glycol methyl ether acrylate, hexyl acrylate, lauryl acrylate, isobutyl acrylate, 2-hydroxyethyl acrylate, tert-butyl acrylate, isooctyl acrylate, tetrahydrofurfuryl acrylate, isodecyl acrylate, 4-hydroxybutyl acrylate, 2-naphthyl acrylate, 2-ethylhexyl acrylate, trimethylsilyl acrylate, 2,2,2-trifluoroethyl acrylate, 4-tert-butylcyclohexyl acrylate, fluorescein O-acrylate, 9-anthracene methyl acrylate, 3-(acryloyloxy)-2-hydroxypropyl methacrylate, allyl methacrylate, benzyl methacrylate, butyl methacrylate, tert-butyl methacrylate, 11-[4-(4-butylphenylazo)phenoxy]undecyl methacrylate, 3-chloro-2-hydroxypropyl methacrylate, cyclohexyl methacrylate, dicyclopentanyl methacrylate, 2-(diethylamino) ethyl methacrylate, diethylene glycol monomethyl ether methacrylate, 2-(dimethylamino)ethyl methacrylate, lauryl methacrylate, 2-ethoxyethyl methacrylate, ethylene glycol monoethyl ether methacrylate, ethyl methacrylate, furfuryl methacrylate, glycidyl methacrylate, 1,1,1,3,3,3-hexafluoroisopropyl methacrylate, hexyl methacrylate, ethylene glycol methacrylate, isobornyl methacrylate, isobutyl methacrylate, 2-isocyanate ethyl methacrylate, isopropyl methacrylate, methacrylic acid, methyl methacrylate, 1H,1H,5H-perfluoropentyl methacrylate, 1,2,2,6,6-pentamethyl-4-piperidyl methacrylate, stearyl methacrylate, N-succinimide methacrylate, 3-sulfopropyl potassium methacrylate, 2,2,3,3-tetrafluoropropyl methacrylate, tetrahydrofurfuryl methacrylate, 2,2,6,6-tetramethyl-4-piperidyl methacrylate, tridecyl methacrylate, 3-(triethoxysilyl) propyl methacrylate, 2,2,2-trifluoroethyl methacrylate, 3-(trimethoxysilyl)propyl methacrylate, 2-(trimethylsilyloxy)ethyl methacrylate, and 3-(tris(trimethylsilyloxy)silyl) propyl methacrylate.

Examples of the (meth)acrylamide monomer include (meth)acrylamides, and derivatives thereof, including, for example, acrylamide, 6-acrylamide hexanoic acid, 2-acrylamide-2-methylpropane sulfonic acid, (3-acrylamidepropyl) trimethylammonium chloride, N-(butoxymethyl)acrylamide, N-tert-butyl acrylamide, trans-3-phenyl acrylamide, N-(1,1-dimethyl-3-oxobutyl) acrylamide, N,N-diethyl acrylamide, N,N'-(1,2-dihydroxyethylene)bisacrylamide, N,N-dimethyl acrylamide, N-[3-(dimethylamino)propyl]acrylamide, N-dodecyl acrylamide, N-ethyl-N-(4-pyridylmethyl)-2-phenyl acrylamide, N-(2-hydroxyethyl) acrylamide, N-(hydroxymethyl)acrylamide, N-isopropyl acrylamide, and N,N'-methylene bis acrylamide.

Examples of the styrene monomer include styrenes, and derivatives thereof, including, for example, styrene, 4-aminostyrene, 4-bromo-β,β-difluorostyrene, 2-bromostyrene, 3-bromostyrene, 4-bromostyrene, 4-tert-butylstyrene, 4-(chloromethyl)styrene, 4-chloro-α-methylstyrene, chloromethylstyrene, 2-chlorostyrene, 3-chlorostyrene, 4-chlorostyrene, 2,6-dichlorostyrene, 4-fluoro-α-methylstyrene, 3-fluorostyrene, 4-fluorostyrene, 4-isopropenyltoluene, 4-methoxystyrene, 2-methylstyrene, 3-methylstyrene, 4-methylstyrene, α-methylstyrene, β-methylstyrene, 4-nitrostyrene, 4-n-octylstyrene, 2,3,4,5,6-pentafluorovinylstyrene, α-(trimethylsilyloxy) styrene, β-styrene sodium sulfonate, 2,4,6-trimethylstyrene, vinyl benzyl cyanide, 2-acetoxystyrene, and 4-acetoxystyrene.

Examples of the vinyl ester monomer include vinyl acetate, vinyl propionate, and vinyl benzoate.

Examples of the nitrile vinyl monomer include acrylonitrile, and methacrylonitrile.

Examples of the vinyl ether monomer include vinyl methyl ether, vinyl ethyl ether, vinyl isobutyl ether, and vinyl phenyl ether.

Examples of the monoolefin monomer include ethylene, propylene, isobutylene, 1-butene, 1-pentene, and 4-methyl-1-pentene.

Examples of the diene monomer include 1,3-butadiene, isoprene, chloroprene, 2,3-dimethyl-1,3-butadiene, 2-methyl-1,3-pentadiene, and 1,3-hexadiene.

The monomers exemplified above may be used either alone or in a combination of two or more.

When the silicon compound is used to polymerize the monomer by living radical polymerization, a transition metal complex may be used as a catalyst when, for example, the radical polymerization initiation group is capable of initiating atom transfer radical polymerization. Preferred as such transition metal complexes are metal complexes having the center metal selected from the Group 7, 8, 9, 10, and 11 elements of the periodic table, more preferably complexes of zero-valent copper, monovalent copper, bivalent ruthenium, bivalent iron, or bivalent nickel. Particularly preferred are monovalent copper complexes, preferably a copper(I) complex with an amine/imine multidentate ligand, for example, such as a halogenated copper (for example, copper chloride)/ amine complex. Azo compounds such as azobisisobutyronitrile (AIBN), and 1,1'-azobis(cyclohexanecarbonitrile) (ABCN), and organic peroxides such as di-tert-butyl peroxide, tert-butyl hydroperoxide, benzoyl peroxide, and methyl ethyl ketone peroxide may be used as polymerization catalysts when, for example, the radical polymerization initiation group is capable of initiating reversible addition-fragmentation chain transfer polymerization.

The molecular weight of the product modified polymer is not particularly limited, and the modified polymer may have various molecular weights as may be decided according to the intended use. For example, when contained in a rubber composition, the polymer obtained by living radical polymerization of the vinyl monomer has a number average molecular weight of preferably 1,000 to 500,000, more preferably 5,000 to 100,000.

The modified polymer may be added to other polymer components such as a rubber component and a plastic component to change the properties of various molded articles. In this case, the content of the modified polymer is not particularly limited, and the modified polymer may be contained in, for example, 0.1 to 100 parts by mass with respect to 100 parts by mass of other polymer components. In one embodiment, a rubber composition contains the modified polymer (preferably, with a vinyl polymer chain as the polymer chain) in 0.1 to 100 parts by mass with respect to 100 parts by mass of the rubber component. The modified polymer has a terminal alkoxysilyl group as noted above, and can react with, for example, the silanol group on a silica surface when silica is contained as a filler in the rubber composition. The modified polymer can thus contribute to improving the properties of the rubber composition. Further, the modified polymer, with the terminal thioether group of silicon compound origin, is believed to have excellent dispersibility for the matrix rubber.

Examples of the rubber component in the rubber composition include natural rubber (NR), isoprene rubber (IR), butadiene rubber (BR), styrene-butadiene rubber (SBR), acrylonitrile-butadiene rubber (NBR), chloroprene rubber (CR), butyl rubber (IIR), halogenated butyl rubber (for example, brominated butyl rubber, chlorinated butyl rubber), and ethylene propylene rubber (EPDM). These may be used either alone or in a combination of two or more. The rubber component is preferably a diene rubber.

The modified polymer content is preferably 0.1 to 100 parts by mass, more preferably 1 to 70 parts by mass, further preferably 5 to 50 parts by mass, particularly preferably 10 to 30 parts by mass with respect to 100 parts by mass of the rubber component.

In addition to the modified polymer, the rubber composition may contain various additives commonly used for rubber compositions. Examples of such additives include fillers (such as silica, and carbon black), silane coupling agents, oil, zinc white, stearic acid, anti-aging agents, waxes, vulcanizing agents, and vulcanization accelerators. The filler content is not particularly limited, and is preferably 10 to 150 parts by mass, more preferably 30 to 100 parts by mass with respect to 100 parts by mass of the rubber component. The filler is preferably silica, and the silica content is at least 50 mass % of the filler.

Examples of the vulcanizing agent include sulfur, and sulfur-containing compounds (for example, sulfur chloride, sulfur dichloride, high molecule polysulfide, morpholine disulfide, and alkylphenol disulfide). These may be used either alone or in a combination of two or more. The vulcanizing agent content is not particularly limited, and is preferably 0.1 to 10 parts by mass, more preferably 0.5 to 5 parts by mass with respect to 100 parts by mass of the rubber component.

Examples of the vulcanization accelerator include various sulfenamide, thiuram, thiazole, and guanidine vulcanization accelerators. These may be used either alone or in a combination of two or more. The vulcanization accelerator content is not particularly limited, and is preferably 0.1 to 7 parts by mass, more preferably 0.5 to 5 parts by mass with respect to 100 parts by mass of the rubber component.

The rubber composition may be produced kneading materials according to an ordinary method, using common mixing machines such as a Banbury mixer, a kneader, and rollers. Use of the product rubber composition is not particularly limited, and the rubber composition may be used in applications such as tires (including treads and sidewalls), conveyer belts, and antivibration rubbers. The rubber composition may be vulcanized and molded at, for example, 140 to 200° C. according to an ordinary method to produce various molded articles.

Complex, Method of Production Thereof, and Molded Article Using Same

The silicon compound according to the present embodiment has an alkoxysilyl group within the molecule, and can serve as a silane coupling agent. The silicon compound can thus be regarded as a polymerization initiator immobilizable on various materials. A polymer-solid substance complex, specifically a complex with a polymer graft chain formed on a solid substance surface can thus be obtained by fixing the silicon compound to a solid substance surface, and polymerizing a monomer through living radical polymerization by using the fixed silicon compound as a polymerization starting point.

Examples of the solid substance include substances made from metals, metallic compounds, inorganic substances (including inorganic compounds), and polymer compounds. The solid substance may have any form, including, for example, molded articles (such as by forging, casting, extrusion, press molding, and injection molding), spheres, fibers, films, woven fabrics, knitted fabrics, nonwoven fabrics, fine particles, and microfibers.

The fine particles have an average particle diameter of 0.1 nm to 1 mm, preferably 1 nm to 100 µm, more preferably 1 nm to 1 µm. As used herein, the fine particle diameter is the average particle diameter (particle diameter of 50% integrated value) as determined by a laser diffraction and scattering method. Fine particles with the primary particle diameters falling in the foregoing ranges may be evaluated with respect to specific surface area by using a BET method (JIS K6217-7) when the particles exist in the form of an aggregation structure such as aggregates. In this case, the BET specific surface area may be 1 to 1,000 $m^2/g$, preferably 20 to 1,000 $m^2/g$, more preferably 40 to 250 $m^2/g$. In the case of microfibers, the average fiber diameter is 0.1 nm to 100 µm, and the average fiber length is 100 nm to 10 mm. Preferably, the average fiber diameter is 1 nm to 10 µm, and the average fiber length is 100 nm to 1 mm. More preferably, the average fiber diameter is 1 nm to 1 µm, and the average fiber length is 100 nm to 100 µm. Here, the average fiber diameter is the arithmetic average of the measured minor axes of 10 randomly selected microfibers from a scanning electron micrograph (SEM). The average fiber length is measured with a fiber length measurement device FS-200 (KAJAANI) according to JIS P8121.

More preferred examples of the solid substance include inorganic fine particles with a hydroxyl group on particle surface, such as silica fine particles, zinc oxide fine particles, titanium oxide fine particles, and barium titanate fine particles. Such inorganic fine particles can easily form a desirable chemical bond with the silicon compound having an alkoxy group, and complex fine particles can be obtained that are strongly bound to the radical polymerization chain.

The method used to fix the silicon compound to a solid substance surface is not particularly limited, and, for example, a common surface treatment method used for silane coupling agents may be used. For example, the silicon compound may be applied to a solid substance surface either directly or in the form of a solution in a suitable solvent. When the solid substance is, for example, a fine particle, the surface treatment may be performed by using a mixture of the solid substance with the silicon compound, which may be mixed either directly or in the form of a solution in a suitable solvent. Specifically, the surface treatment may be a dry process in which the silicon compound is sprayed onto the solid substance either directly or in the form of a solution in a suitable solvent, or a wet process in which the silicon compound is added and stirred in a slurry prepared by adding, for example, water to the solid substance.

As used herein, "fixing" may be chemical bonding of the silicon compound to a solid substance surface by, for example, hydrolysis of the alkoxy group, or physical bonding, such as hydrogen bonding, trapping the silicon compound inside solid surface pores. Fixing may be confirmed by washing the fixed surface with an organic solvent or the like, and determining the presence or absence of the silicon compound elements thereon by using a technique such as energy dispersive X-ray spectroscopy (EDX) or X-ray photoelectron spectroscopy (XPS).

When the silicon compound fixed solid substance is used to polymerize monomer from the silicon compound through living radical polymerization, a vinyl monomer or a diene monomer may be polymerized by living radical polymerization using a catalyst such as the transition metal complex, the azo compound, and the organic peroxide, as described above. The vinyl monomer and the diene monomer are as exemplified above.

In the complex obtained as above, the amount of the polymer graft chain formed by living radical polymerization of the monomer is preferably 5 to 1,000 parts by mass with respect to 100 parts by mass of the solid substance (particularly preferably, inorganic fine particles). The amount of polymer graft chain is more preferably 30 to 500 parts by mass, further preferably 50 to 300 parts by mass with respect to 100 parts by mass of the solid substance.

The molded article of the present embodiment comprises the complex. To be more specific, complex fine particles in which a thermoplastic polymer graft chain is formed on raw material solid substance fine particles are used as the complex, and molded into a predetermined shape by powder molding or injection molding to obtain a molded article of the complex fine particles.

Use of the complex and the molded article is not particularly limited, and these may be used as, for example, reinforcing agents contained in rubber compositions and plastic compositions; polymer colloidal crystals used as nanooptical materials in the field of optical communications, color video devices, high-power lasers, and the like; or electrolyte films or dielectric materials of lithium ion batteries or the like.

Rubber or Plastic Reinforcing Agent, Method of Production Thereof, and Rubber or Plastic Composition The rubber or plastic reinforcing agent according to the present embodiment is obtained by fixing the silicon compound to a solid substance surface, and polymerizing a radically polymerizable monomer through living radical polymerization by using the living radical polymerization initiation group as a starting point of polymerization.

The solid substance used to fix the silicon compound is preferably a fine particle or a microfiber, so that these fine particles and microfibers can disperse in and reinforce the rubber or plastic matrix. The solid substance may be made of materials, for example, such as metals, metallic compounds, inorganic substances (including inorganic compounds), and polymer compounds, preferably with a surface hydroxyl group. In this way, the silicon compound, with the alkoxysilyl group contained in the molecule, can more strongly fix by reacting with the hydroxyl group on a solid substance surface by, for example, hydrolysis of the alkoxy group.

The solid substance fine particles and microfibers are same as the solid substance used for the complex in terms of average particle diameter, the BET specific surface area of an aggregation structure, average microfiber diameter, and average microfiber length. Preferred as the solid substance are inorganic fine particles with a surface hydroxyl group, such as silica fine particles, zinc oxide fine particles, titanium oxide fine particles, and barium titanate fine particles, as with the case of the complex.

In a preferred embodiment, silica may be used as the solid substance. It is believed that a polymer grafted silica with the established polymer phase after the graft polymerization from the silica surface has improved dispersibility for the rubber matrix due to the presence of the polymer phase when contained in a rubber composition. It is also believed that the direct bonding between the polymer chain and the silica establishes and maintains a hard resin phase even after these are mixed with rubber, and increases reinforcement. This makes it possible to improve elasticity while suppressing heat generation.

The method of fixing the silicon compound to a solid substance surface, the form of fixing, and the method of confirming fixing of the silicon compound are as described in conjunction with the complex.

The solid substance with the fixed silicon compound is used to polymerize monomer from the silicon compound through living radical polymerization. A reinforcing agent formed as a complex with the polymer graft chain formed on a solid substance surface can then be obtained (hereinafter, such a reinforcing agent also will be called polymer grafted reinforcing agent). In the living radical polymerization of monomer from the silicon compound, the monomer may be at least one selected from the group consisting of a vinyl monomer and a diene monomer, and the polymerization may be performed with a catalyst such as the transition metal complex, the azo compound, and the organic peroxide, as described above. The vinyl monomer and the diene monomer are as exemplified above.

In the polymer grafted reinforcing agent, the amount of polymer graft chain is preferably 5 to 1,000 parts by mass with respect to 100 parts by mass of the solid substance. More preferably, the polymer graft chain amount is 30 to 500 parts by mass, further preferably 50 to 300 parts by mass with respect to 100 parts by mass of the solid substance.

In the polymer grafted reinforcing agent, the glass transition point (Tg) of the polymer graft chain is not particularly limited, and may be appropriately set within a range of, for example, −100° C. to 150° C. For example, when contained in a rubber composition, the polymer grafted reinforcing agent can preferably be used for tread rubbers that require high gripping performance, and energy absorbing rubbers such as antivibration rubber when the polymer graft chain Tg is in the vicinity of 10° C. to 70° C., because such a glass transition point can effectively increase tan δ near 60° C. When the polymer graft chain Tg is in a high-temperature range of 80° C. or higher, tan δ near room temperature can be kept low while increasing elastic modulus, making the polymer grafted reinforcing agent preferable for use in, for example, fuel-efficient tires. When the polymer graft chain Tg is in a low-temperature range of −10° C. or less, tan δ can be increased while keeping the elastic modulus low in the vicinity of 0° C. This makes the polymer grafted reinforcing agent preferable for use in, for example, rubbers for high gripping tires and winter tires. The polymer graft chain Tg can be set by forming the polymer graft chain with different monomers.

The polymer grafted reinforcing agent is added to a rubber component or a plastic component to reinforce a rubber composition or a plastic composition. The polymer grafted reinforcing agent improves the dispersibility of the reinforcing agent (solid substance) in the rubber matrix or plastic matrix, and can improve the properties of a rubber composition or a plastic composition. Further, because the polymer grafted reinforcing agent has the grafted polymer chain fixed on the solid substance surface, the polymer graft chain can remain even after the polymer grafted reinforcing agent is mixed with a rubber matrix or a plastic matrix. This helps assist the high elasticity effect.

The rubber composition according to the present embodiment may contain the polymer grafted reinforcing agent in 1 to 200 parts by mass with respect to 100 parts by mass of the rubber component. The content of the polymer grafted reinforcing agent is more preferably 10 to 150 parts by mass, further preferably 20 to 100 parts by mass. The rubber component is as exemplified above in conjunction with the use of the modified polymer as a rubber composition. Preferably, a diene rubber is used.

In addition to the polymer grafted reinforcing agent, the rubber composition may contain various additives commonly used for rubber compositions. Examples of such additives include reinforcing fillers (such as untreated silica and carbon black), silane coupling agents, oil, zinc white, stearic acid, anti-aging agents, waxes, vulcanizing agents, and vulcanization accelerators. Examples of the vulcanizing agents, the vulcanizing agent content, examples of the vulcanization accelerators, the vulcanization accelerator content, the rubber composition producing method, use of the rubber composition, and the rubber molded article producing method using the rubber composition are as described in conjunction with the use of the modified polymer as a rubber composition.

The plastic composition according to the present embodiment may contain the polymer grafted reinforcing agent in 1 to 200 parts by mass with respect to 100 parts by mass of the plastic component. The polymer grafted reinforcing agent content is more preferably 10 to 150 parts by mass, further preferably 20 to 100 parts by mass.

Examples of the plastic component in the plastic composition include polyolefin, polystyrene, polyacrylate, polymethacrylate, polyester, polyamide, polyurethane, polycarbonate, and polyimide. These may be used either alone or in a combination of two or more.

In addition to the polymer grafted reinforcing agent, the plastic composition may contain various additives commonly used for plastic compositions. Examples of such additives include antioxidants, plasticizers, crosslinkers, inorganic particles, glass fibers, and organic fibers.

The plastic composition may be produced by being kneaded according to an ordinary method, using common mixing machines such as mixers and kneaders. Use of the plastic composition is not particularly limited, and the plastic composition may be used in applications such as in films, containers, coating agents, adhesives, automobile components, and heat insulating materials. The plastic composition may be used to produce various plastic molded articles by using techniques such as injection molding and compression molding according to an ordinary method.

EXAMPLES

Examples of the present invention are described below. It should be noted that the present invention is not limited by the following Examples.

Synthesis of Silicon Compound

Example 1

Synthesis of 6-(3-(triethoxysilyl)propylthio)hexyl 2-bromo-2-methylpropanate

5-Hexen-1-ol (42.6 g), triethylamine (45.8 g), and tetrahydrofuran (0.8 L) were mixed. After ice cooling, 2-bromoisobutyryl bromide (100 g) was dropped. The reaction liquid was stirred at 4° C. for 3 hours, and then at room temperature for 15 hours. The reaction liquid was then filtered, concentrated with an evaporator, and dissolved in diethyl ether (300 mL). The solution was washed with a 1N hydrochloric acid solution (2×300 mL), a saturated sodium bicarbonate solution (2×300 mL), and distilled water (2×300 mL), in this order. After that, the organic layer was dried over sodium sulfate, filtered, and concentrated with an evaporator. The product was then purified through a silica gel column (developing solvent: hexane/ethyl acetate=15/1), and concentrated to give 74.2 g of 5-hexenyl 2-bromo-2-methylpropanate of the following chemical formula (compound 1).

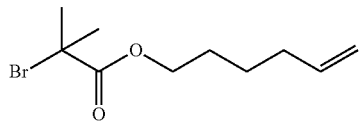

Compound 1 (10.1 g), 3-mercaptopropyltriethoxysilane (9.58 g; Tokyo Chemical Industry Co., Ltd.), AIBN (0.194 g), and toluene (20 g) were mixed. After bubbling with nitrogen gas for 30 min, the reaction solution was maintained at 70° C. for 3 hours, and concentrated with an evaporator to give 17.2 g of 6-(3-(triethoxysilyl)propylthio)hexyl 2-bromo-2-methylpropanate of the chemical formula below (compound 2; yield: 88%).

NMR identified the product as the compound of the chemical formula below.

$^1$H-NMR (400 MHz, TMS standard=0.0 ppm): 1.93 (s, 6H, $(CH_3)_2BrC-$), 4.17 (t, 2H, $-(O=C)-O-CH_2-$), 1.70 (m, 2H, $-(O=C)-O-CH_2-CH_2-$), 1.43 (t, 4H, $-(O=C)-O-CH_2-CH_2-CH_2-CH_2-$), 1.60 (t, 2H, $O=C-O-CH_2-CH_2-CH_2-CH_2-CH_2-$), 2.5 (t, 2H, $-CH_2-S-CH_2-$), 2.53 (t, 2H, $-CH_2-S-CH_2-$), 1.69 (m, 2H, $-CH_2-S-CH_2-CH_2-$), 0.74 (t, 2H, $-CH_2-Si-(O-CH_2-CH_3)_3$), 3.82 (q, 6H, $-CH_2-Si-(O-CH_2-CH_3)_3$), 1.23 (t, 9H, $-CH_2-Si-(O-CH_2-CH_3)_3$).

$^{13}$C-NMR (400 MHz, TMS standard=0.0 ppm): 30.9 $((CH_3)_2BrC-)$, 55.9 $((CH_3)_2BrC-)$, 171.5 $(-(O=C)-O-CH_2-)$, 65.9 $(-(O=C)-O-CH_2-)$, 28.3 $(-(O=C)-O-CH_2-CH_2-)$, 25.9 $(-(O=C)-O-CH_2-CH_2-CH_2-)$, 28.4 $(-(O=C)-O-CH_2-CH_2-CH_2-CH_2-)$, 29.6 $(-(O=C)-O-CH_2-CH_2-CH_2-CH_2-CH_2-)$, 32.0 $(-CH_2-S-CH_2-)$, 35.3 $(-CH_2-S-CH_2-)$, 23.2 $(-CH_2-S-CH_2-CH_2-)$, 10.3 $(-CH_2-Si-(O-CH_2-CH_3)_3)$, 58.4 $(-CH_2-Si-(O-CH_2-CH_3)_3)$, 18.3 $(-CH_2-Si-(O-CH_2-CH_3)_3)$.

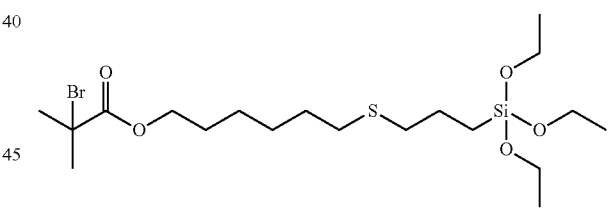

Example 2

3-(3-(Triethoxysilyl)propylthio)propyl 2-bromo-2-methylpropanate

Allyl 2-(2-bromo-2-methyl)propionate (1.5 g; Sigma Aldrich), 3-mercaptopropyltriethoxysilane (1.73 g), AIBN (0.036 g), and toluene (20 g) were mixed. After bubbling with nitrogen gas for 30 min, the reaction solution was maintained at 70° C. for 3 hours, and concentrated with an evaporator to give 2.95 g of 3-(3-(triethoxysilyl)propylthio) propyl 2-bromo-2-methylpropanate of the chemical formula below (compound 3; yield: 91%).

NMR identified the product as the compound of the chemical formula below.

$^1$H-NMR (400 MHz, TMS standard=0.0 ppm): 1.93 (s, 6H, $(CH_3)_2BrC-$), 4.27 (t, 2H, $-(O=C)-O-CH_2-$), 1.97 (m, 2H, $-(O=C)-O-CH_2-CH_2-$), 2.61 (t, 2H, —CH$_2$—S—CH$_2$—), 2.55 (t, 2H, —CH$_2$—S—CH$_2$—), 1.71 (m, 2H, —CH$_2$—S—CH$_2$—CH$_2$—), 0.74 (t, 2H, —CH$_2$—Si—(O—CH$_2$—CH$_3$)$_3$), 3.82 (q, 6H, —CH$_2$—Si—(O—CH2-CH$_3$)$_3$), 1.23 (t, 9H, —CH$_2$—Si—(O—CH$_2$—CH$_3$)$_3$).

$^{13}$C-NMR (400 MHz, TMS standard=0.0 ppm): 30.8 ((CH$_3$)$_2$BrC—), 55.9 ((CH$_3$)$_2$BrC—), 171.5 (—(O=C)—O—CH$_2$—), 64.6 (—(O=C)—O—CH$_2$—), 28.6 (—(O=C)—O—CH$_2$—CH$_2$—), 28.3 (—CH$_2$—S—CH$_2$—), 35.2 (—CH$_2$—S—CH$_2$—), 23.2 (—CH$_2$—S—CH$_2$—CH$_2$—), 9.94 (—CH$_2$—Si—(O—CH$_2$—CH$_3$)$_3$), 58.4 (—CH$_2$—Si—(O—CH$_2$—CH$_3$)$_3$), 18.4 (—CH$_2$—Si—(O—CH$_2$—CH$_3$)$_3$).

2H, —CH$_2$—Si—(O—CH$_2$—CH$_3$)$_3$), 3.82 (q, 6H, —CH$_2$—Si—(O—CH$_2$—CH$_3$)$_3$), 1.23 (t, 9H, —CH$_2$—Si—(O—CH$_2$—CH$_3$)$_3$).

$^{13}$C-NMR (400 MHz, TMS standard=0.0 ppm): 30.8 ((CH$_3$)$_2$BrC—), 56.4 ((CH$_3$)$_2$BrC—), 172.1 (—(O=C)—O—CH$_2$—), 66.2 (—(O=C)—O—CH$_2$—), 29.0 to 29.5 (—(O=C)—O—CH$_2$—(CH$_2$)$_8$—), 29.8 (—(O=C)—O—CH$_2$—(CH$_2$)$_8$—CH$_2$), 32.0 (—CH$_2$—S—CH$_2$—), 35.3 (—CH$_2$—S—CH$_2$—), 23.3 (—CH$_2$—S—CH$_2$—CH$_2$—), 9.7 (—CH$_2$—Si—(O—CH$_2$—CH$_3$)$_3$), 58.4 (—CH$_2$—Si—(O—CH$_2$—CH$_3$)$_3$), 18.4 (—CH$_2$—Si—(O—CH$_2$—CH$_3$)$_3$).

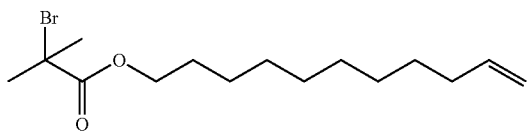 [SMILES: C=CCCCCCCCCCOC(=O)C(C)(C)Br]

Example 4

Synthesis of 6-(3-(triethoxysilyl)propylthio)hexyl 2-iodo-2-methylpropanate

The 6-(3-(triethoxysilyl)propylthio)hexyl 2-bromo-2-methylpropanate (5 g) obtained through the procedures of Example 1 was mixed with sodium iodide (20 g) and dry acetone (100 mL), and the mixture was allowed to react in a nitrogen atmosphere at 75° C. for 10 hours. After the reaction, extraction was performed to give 6-(3-(triethoxysilyl)propylthio)hexyl 2-iodo-2-methylpropanate of the chemical formula below (compound 6).

NMR identified the product as the compound of the chemical formula below.

$^1$H-NMR (400 MHz, TMS standard=0.0 ppm): 2.2 (s, 6H, (CH$_3$)$_2$IC—), 4.17 (t, 2H, —(O=C)—O—CH$_2$—), 1.70 (m, 2H, —(O=C)—O—CH$_2$—CH$_2$—), 1.43 (t, 4H, —(O=C)—O—CH$_2$—CH$_2$—CH$_2$—CH$_2$—), 1.60 (t, 2H, O=C—O—CH$_2$—CH$_2$—CH$_2$—CH$_2$—CH$_2$—), 2.5 (t, 2H, —CH$_2$—S—CH$_2$—), 2.53 (t, 2H, —CH$_2$—S—CH$_2$—), 1.69 (m, 2H, —CH$_2$—S—CH$_2$—CH$_2$—), 0.74 (t, 2H, —CH$_2$—Si—(O—CH$_2$—CH$_3$)$_3$), 3.82 (q, 6H, —CH$_2$—Si—(O—CH$_2$—CH$_3$)$_3$), 1.23 (t, 9H, —CH$_2$—Si—(O—CH$_2$—CH$_3$)$_3$).

$^{13}$C-NMR (400 MHz, TMS standard=0.0 ppm): 27.5 ((CH$_3$)$_2$IC—), 57.4 ((CH$_3$)$_2$IC—), 171.5 (—(O=C)—O—CH$_2$—), 65.9 (—(O=C)—O—CH$_2$—), 28.3 (—(O=C)—O—CH$_2$—CH$_2$—), 25.9 (—(O=C)—O—CH$_2$—CH$_2$—CH$_2$—), 28.4 (—(O=C)—O—CH$_2$—CH$_2$—CH$_2$—CH$_2$—), 29.6 (—(O=C)—O—CH$_2$—CH$_2$—CH$_2$—CH$_2$—CH$_2$—), 32.0 (—CH$_2$—S—CH$_2$—), 35.3 (—CH$_2$—S—CH$_2$—), 23.2 (—CH$_2$—S—CH$_2$—CH$_2$—), 10.3 (—CH$_2$—Si—(O—CH$_2$—CH$_3$)$_3$), 58.4 (—CH$_2$—Si—(O—CH$_2$—CH$_3$)$_3$), 18.3 (—CH$_2$—Si—(O—CH$_2$—CH$_3$)$_3$).

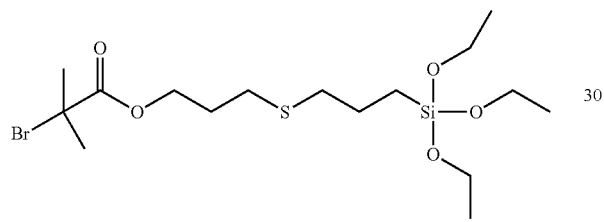

Example 3

11-(3-(Triethoxysilyl)propylthio)undecyl 2-bromo-2-methylpropanate

10-Undecenyl 2-bromo-2-methylpropanate of the following chemical formula (compound 4) was obtained in the same manner as in Example 1, except for using 10-undecen-1-ol in place of 5-hexen-1-ol.

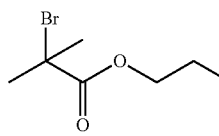

The 10-undecenyl 2-bromo-2-methylpropanate was reacted with 3-mercaptopropyltriethoxysilane in the same manner as in Example 1 to give 11-(3-(triethoxysilyl)propylthio)undecyl 2-bromo-2-methylpropanate of the chemical formula below (compound 5).

NMR identified the product as the compound of the chemical formula below.

$^1$H-NMR (400 MHz, TMS standard=0.0 ppm): 1.92 (s, 6H, (CH$_3$)$_2$BrC—), 4.16 (t, 2H, —(O=C)—O—CH$_2$—), 1.28 to 1.38 (m, 16H, —(O=C)—O—CH$_2$—(CH$_2$)$_8$—), 1.56 (m, 16H, —(O=C)—O—CH$_2$—(CH$_2$)$_8$—CH$_2$—), 2.5 (t, 2H, —CH$_2$—S—CH$_2$—), 2.53 (t, 2H, —CH$_2$—S—CH$_2$—), 1.70 (m, 2H, —CH$_2$—S—CH$_2$—CH$_2$—), 0.73 (t,

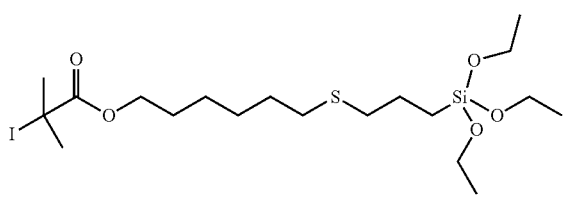 [SMILES: CCO[Si](CCCSCCCCCCOC(=O)C(C)(C)I)(OCC)OCC]

Synthesis of Polymer Grafted Reinforcing Agent

Example 5

Silica (35 g; Tosoh Silica Corporation "Nipsil AQ"; BET specific surface area=205 m²/g), 28 mass % of ammonia water (66 g), and ethanol (1,000 mL) were mixed. After stirring the mixture for 1 hour, the compound 2 (6-(3-(triethoxysilyl)propylthio)hexyl 2-bromo-2-methylpropanate; 10 g) was dropped, and the mixture was stirred at room temperature for 16 hours. The resulting solution was centrifuged to collect silica, and the silica was washed with ethanol and anisole to give silica fixing the compound 2 to the particle surface (polymerization initiator introduced silica; 28 g).

The polymerization initiator introduced silica (22.9 g) was mixed with benzyl methacrylate (200 g), ethyl 2-bromobutyrate (1.14 g), 4,4'-dinonyl-2,2'-bipyridyl (4.54 g), and anisole (300 g). After 1.5-hour nitrogen bubbling, copper chloride(I) (0.56 g) was added to the reaction solution, and the mixture was maintained at 50° C. for 5 hours. The resulting solution was centrifuged to separate the solid phase, which was then washed with anisole, and dried to give a polymer grafted silica (43 g) as a complex of silica and polymer graft chain (reinforcing agent 1).

Examples 6 to 8

Reinforcing agents 2 to 4 were obtained in the same manner as in Example 5, except that the charging ratio (molar ratio) of the monomer (benzyl methacrylate) with respect to the polymerization initiator was changed as shown in Table 1.

Example 9

A polymer grafted silica as a reinforcing agent 5 was obtained in the same manner as in the synthesis of the reinforcing agent 1, except that the monomer was changed from benzyl methacrylate to methyl methacrylate.

Example 10

A polymer grafted silica as a reinforcing agent 6 was obtained in the same manner as in the synthesis of the reinforcing agent 1, except that the monomer was changed from benzyl methacrylate to tridecyl methacrylate.

Measurement of Polymer Graft Amount in Reinforcing Agent

Polymer graft amounts were calculated from the TGA measurement results (rate of temperature increase 5° C./min, temperature range 50° C. to 500° C.), using the following formula (A). The results are presented in Table 1.

$$P = (W_{initial} - W_{500° C.}/0.9)/(W_{500° C.}/0.9) \quad \text{Formula (A)}$$

P: Polymer graft mass per unit mass of silica
$W_{initial}$: Initial mass at the start of TGA measurement (mg)
$W_{500° C.}$: Residual mass at 500° C. (mg)

Measurement of Polymer Graft Chain Glass Transition Point

DSC measurement was performed for the reinforcing agent to determine the glass transition point (Tg) of the polymer graft chain. The measurement was made in a temperature range of −100° C. to 150° C. at a rate of temperature increase of 20° C./min.

TABLE 1

| | Monomer | Molar ratio of monomer/ polymerization initiating agent | Polymer graft mass per unit mass of silica | Tg (° C.) |
|---|---|---|---|---|
| Reinforcing agent 1 | Benzyl methacrylate | 200 | 1.1 | 50 |
| Reinforcing agent 2 | Benzyl methacrylate | 75 | 0.5 | 49 |
| Reinforcing agent 3 | Benzyl methacrylate | 100 | 0.7 | 48 |
| Reinforcing agent 4 | Benzyl methacrylate | 400 | 1.8 | 51 |
| Reinforcing agent 5 | Methyl methacrylate | 200 | 1.0 | 107 |
| Reinforcing agent 6 | Tridecyl methacrylate | 200 | 1.0 | −47 |

The TGA measurement of the complex fine particles confirmed the presence of a graft polymer chain. Further, as can be seen in Table 1, the monomer charging ratio was proportional to the polymer graft chain amount, demonstrating that the polymerization occurred in a living fashion from the silica surface.

Example 11

Zinc Oxide Complex

Zinc oxide (100 g; Sakai Chemical Industry Co., Ltd. "FINEX-30"), 28 mass % of ammonia water (66 g), and ethanol (1,000 mL) were mixed. After stirring the mixture for 1 hour, the compound 2 (6-(3-(triethoxysilyl)propylthio) hexyl 2-bromo-2-methylpropanate; 10 g) was dropped, and the mixture was stirred at room temperature for 16 hours. The resulting solution was centrifuged to collect zinc oxide, and the zinc oxide was washed with ethanol and anisole to give zinc oxide fixing the compound 2 to the particle surface (polymerization initiator introduced zinc oxide; 82 g).

The polymerization initiator introduced zinc oxide (62 g), benzyl methacrylate (200 g), ethyl 2-bromobutyrate (1.14 g), 4,4'-dinonyl-2,2'-bipyridyl (4.54 g), and anisole (300 g) were mixed. After 1.5-hour nitrogen bubbling, copper chloride(I) (0.56 g) was added to the reaction solution, and the mixture was maintained at 50° C. for 5 hours. The resulting solution was centrifuged to separate the solid phase, which was then washed with anisole, and dried to give polymer grafted zinc oxide (75.9 g) as a reinforcing agent 7. The reinforcing agent 7 was measured for polymer graft amount in the same manner as for the reinforcing agent 1. The result is presented in Table 2.

TABLE 2

| | Reinforcing agent 7 |
|---|---|
| Molar ratio of monomer/polymerization initiating agent | 200 |
| Polymer graft mass per unit mass of zinc oxide | 0.38 |

Example 12

Barium Titanate Complex

Barium titanate (100 g: Sakai Chemical Industry Co., Ltd. "BT01"), 28 mass % ammonia water (66 g), and ethanol (1,000 mL) were mixed. After stirring the mixture for 1 hour, the compound 2 (6-(3-(triethoxysilyl)propylthio)hexyl 2-bromo-2-methylpropanate; 10 g) was dropped, and the mixture was stirred at room temperature for 16 hours. The resulting solution was centrifuged to collect barium titanate, and the barium titanate was washed with ethanol and anisole to give barium titanate fixing the compound 2 to the particle surface (polymerization initiator introduced barium titanate; 85 g).

The polymerization initiator introduced barium titanate (68 g), benzyl methacrylate (200 g), ethyl 2-bromobutyrate (1.14 g), 4,4'-dinonyl-2,2'-bipyridyl (4.54 g), and anisole (300 g) were mixed. After 1.5-hour nitrogen bubbling, copper chloride(I) (0.56 g) was added to the reaction solution, and the mixture was maintained at 50° C. for 5 hours. The resulting solution was centrifuged to separate the solid phase, which was then washed with anisole, and dried to give polymer grafted barium titanate (82 g) as a reinforcing agent 8. The reinforcing agent 8 was measured for polymer graft amount in the same manner as for the reinforcing agent 1. The result is presented in Table 3.

TABLE 3

| | Reinforcing agent 8 |
|---|---|
| Molar ratio of monomer/polymerization initiating agent | 200 |
| Polymer graft mass per unit mass of barium titanate | 0.36 |

Synthesis of Modified Polymer

Example 13

Benzyl methacrylate (30 g), the compound 2 (6-(3-(triethoxysilyl)propylthio)hexyl 2-bromo-2-methylpropanate; 0.415 g), 4,4'-dinonyl-2,2'-bipyridyl (0.70 g), and anisole (30 g) were mixed. After 1.5-hour nitrogen bubbling, copper chloride(I) (0.081 g) was added to the reaction solution, and the mixture was maintained at 50° C. for 5 hours. The resulting solution was purified by ethanol reprecipitation to give polybenzyl methacrylate (polymer E1).

The polymer E1 was a modified polymer that had an alkoxysilyl group and a thioether group of compound 2 origin at a molecular end, and the structure of the formula (4-4) above ($R^1$=ethyl, $R^7$=$R^8$=methyl, a=6, m=n=3). The number average molecular weight was 19,000, the weight average molecular weight was 23,000, and the molecular weight distribution was 1.24.

On the other hand, in a common radical polymerization (benzyl methacrylate (30 g), AIBN (0.07 g), and anisole (30 g) were mixed, and polymerized at 70° C. for 3 hours after 1.5-hour nitrogen bubbling), the resulting polymer had a number average molecular weight of 34,000, a weight average molecular weight of 75,000, and a molecular weight distribution of 2.2. As demonstrated by the narrow molecular weight distribution of the polymer E1 of Example 13, the polymerization initiator by compound 2 was found to be capable of living radical polymerization.

The alkoxysilyl group and the thioether group at the molecular end were confirmed by $^1$H-NMR and $^{13}$C-NMR.

The number average molecular weight (Mn), the weight average molecular weight (Mw), and the molecular weight distribution (Mw/Mn) were determined by gel permeation chromatography (GPC) in terms of polystyrene. Specifically, 0.2 mg of a sample dissolved in 1 ml of THF was used for the measurement. The sample was filtered using a Shimadzu "LC-20DA", passed through a column (Polymer Laboratories "PL Gel3 μm Guard×2") at 40° C. and a flow rate of 0.7 mL/min, and detected with a Spectra System "RI Detector".

Example 14

A modified polymer polymethyl methacrylate (polymer E2) having an alkoxysilyl group and a thioether group at a molecular end was obtained in the same manner as for the polymer E1, except that the monomer was changed from benzyl methacrylate to methyl methacrylate. The polymer E2 had a number average molecular weight of 15,000, a weight average molecular weight of 18,000, and a molecular weight distribution of 1.2.

Example 15

A modified polymer polytridecyl methacrylate (polymer E3) having an alkoxysilyl group and a thioether group at a molecular end was obtained in the same manner as for the polymer E1, except that the monomer was changed from benzyl methacrylate to tridecyl methacrylate. The polymer E3 had a number average molecular weight of 23,000, a weight average molecular weight of 29,000, and a molecular weight distribution of 1.26.

Comparative Example 1

Benzyl methacrylate (30 g), ethyl 2-bromobutyrate (0.66 g), 4,4'-dinonyl-2,2'-bipyridyl (1.4 g), and anisole (30 g) were mixed. After 1.5-hour nitrogen bubbling, copper chloride(I) (0.17 g) was added to the reaction solution, and the mixture was maintained at 50° C. for 5 hours. The resulting solution was purified by ethanol reprecipitation to give unmodified polybenzyl methacrylate (polymer C1). The polymer C1 had a number average molecular weight of 19,000, a weight average molecular weight of 23,000, and a molecular weight distribution of 1.24.

Comparative Example 2

An unmodified polymethyl methacrylate (polymer C2) was obtained in the same manner as for the polymer C1, except that the monomer was changed from benzyl methacrylate to methyl methacrylate. The polymer C2 had a number average molecular weight of 16,000, a weight average molecular weight of 19,000, and a molecular weight distribution of 1.2.

Comparative Example 3

An unmodified polytridecyl methacrylate (polymer C3) was obtained in the same manner as for the polymer C1, except that the monomer was changed from benzyl methacrylate to tridecyl methacrylate. The polymer C3 had a number average molecular weight of 24,000, a weight average molecular weight of 30,000, and a molecular weight distribution of 1.25.

Evaluation of Rubber Composition

Examples 16 to 18, and Comparative Examples 4 and 5

As a first mixing step, compounding agents other than sulfur and a vulcanization accelerator were added to a rubber component in the formulation (parts by mass) presented in Table 4, and the mixture was kneaded (discharge temperature=160° C.), using a Banbury mixer. In the final mixing step, sulfur and a vulcanization accelerator were added to the kneaded product, and kneaded (discharge temperature=90° C.) to prepare a rubber composition. Details of each component shown in Table 4 are as follows.

SBR: Styrene-butadiene rubber, JSR Corporation "SBR1502"

Silica: Tosoh Silica Corporation "Nipsil AQ"

Silane coupling agent: bis(3-Triethoxysilylpropyl)tetrasulfide, Evonik Degussa "Si69"

Zinc white: Mitsui Mining & Smelting Co., Ltd. "Zinc White Type 1"

Anti-aging agent: Ouchi Shinko Chemical Industrial Co., Ltd. "Nocrac 6C"

Stearic acid: Kao Corporation "Lunac S-20"

Sulfur: Hosoi Kagaku Kogyo "Powder Sulfur for Rubbers (150 mesh)"

Vulcanization accelerator: Ouchi Shinko Chemical Industrial Co., Ltd. "Nocceler CZ"

Secondary vulcanization accelerator: Ouchi Shinko Chemical Industrial Co., Ltd. "Nocceler D"

Each rubber composition was vulcanized at 160° C.×20 min to produce a test piece of a predetermined shape. The test piece was then used to determine 25° C. dynamic elastic modulus E* and tan δ, and 60° C. dynamic elastic modulus E* and tan δ. The following measurement methods were used.

25° C. Dynamic elastic modulus E*:

Dynamic elastic modulus E* was measured under 50 Hz frequency, 10% static strain, 2% dynamic strain, and 25° C. temperature conditions using a UBM rheospectrometer E4000.

25° C. tan δ:

Loss factor tan δ was measured under 50 Hz frequency, 10% static strain, 2% dynamic strain, and 25° C. temperature conditions using a UBM rheospectrometer E4000.

60° C. Dynamic elastic modulus E* and 60° C. tan δ:

Measurements were made in the same manner as in the 25° C. dynamic elastic modulus E* and 25° C. tan δ measurements, except that the temperature was changed to 60° C.

The results are presented in Table 4. Comparative Example 5 with the addition of the unmodified polymer C1 had increased dynamic elastic modulus and tan δ values compared to the control Comparative Example 4. Example 16 with the modified polymer E1 had greatly increased dynamic elastic modulus and tan δ values compared to Comparative Example 4. Example 17 with the polymer grafted silica of the reinforcing agent 1 had a higher dynamic elastic modulus than Example 16. Example 18 with the reinforcing filler solely made of the polymer grafted silica of the reinforcing agent 2 had an even greater dynamic elastic modulus than Example 17. In Comparative Example 5 and Examples 16 to 18, the rubber mixture contained substantially equal amounts of the silica component and the polybenzyl methacrylate component (grafted polybenzyl methacrylate in the reinforcing agents 1 and 2). However, in contrast to Comparative Example 5 in which the polybenzyl methacrylate is believed to exist as an isolation phase, the dynamic elastic modulus and tan δ effectively increased in Examples 17 and 18 because of the complete binding of the polybenzyl methacrylate to the silica. In Example 16, the dynamic elastic modulus and tan δ increased more efficiently than in Comparative Example 5 because the polybenzyl methacrylate component had a terminal ethoxysilyl group capable of reacting with the silanol group on silica surface, and existed in higher concentration in the vicinity of the silica. Such rubbers showing a large energy loss in the vicinity of 60° C. are preferred for use as tread rubber mixtures that require high grip performance, and energy absorbing rubbers.

TABLE 4

| | Com. Ex. 4 | Com. Ex. 5 | Ex. 16 | Ex. 17 | Ex. 18 |
|---|---|---|---|---|---|
| Formulation (parts by mass) | | | | | |
| SBR | 100 | 100 | 100 | 100 | 100 |
| Silica | 50 | 50 | 50 | 25 | |
| Silane coupling agent | 2 | 2 | 2 | 2 | 2 |
| Reinforcing agent 1 | | | | 50 | |
| Reinforcing agent 2 | | | | | 75 |
| Polymer E1 (modified) | | | 25 | | |
| Polymer C1 (unmodified) | | 25 | | | |
| Zinc white | 2 | 2 | 2 | 2 | 2 |
| Anti-aging agent | 2 | 2 | 2 | 2 | 2 |
| Stearic acid | 2 | 2 | 2 | 2 | 2 |
| Sulfur | 1.8 | 1.8 | 1.8 | 1.8 | 1.8 |
| Vulcanization accelerator | 1.8 | 1.8 | 1.8 | 1.8 | 1.8 |
| Secondary vulcanization accelerator | 1.5 | 1.5 | 1.5 | 1.5 | 1.5 |
| Physical properties | | | | | |
| 25° C. dynamic elastic modulus E* (Mpa) | 7.9 | 12.6 | 15.1 | 18.0 | 19.5 |
| 25° C. tan δ | 0.19 | 0.21 | 0.23 | 0.23 | 0.24 |
| 60° C. dynamic elastic modulus E* (Mpa) | 6.6 | 9.8 | 10.0 | 12.0 | 13.5 |
| 60° C. tan δ | 0.16 | 0.19 | 0.27 | 0.27 | 0.29 |

Examples 19 and 20, and Comparative Example 6

Rubber compositions were prepared in the same manner as in Example 16 in the formulations (parts by mass) presented in Table 5, using a Banbury. A test piece produced from each rubber composition was then used to determine 25° C. dynamic elastic modulus E* and tan δ.

The results are presented in Table 5. Comparative Example 6 with the unmodified polymethyl methacrylate of the polymer C2 had a higher dynamic elastic modulus than the control Comparative Example 4. Example 19 with the modified polymethyl methacrylate of the polymer E2 had an even higher dynamic elastic modulus. The dynamic elastic modulus was even higher in Example 20 in which the polymer grafted silica of the reinforcing agent 5 was contained. On the other hand, tan δ showed only a limited increase in the vicinity of room temperature because of the polymethyl methacrylate glass transition point being in a high-temperature region. The rubber compositions of Examples 19 and 20 are thus preferred for applications such as rubbers for fuel-efficient tires.

TABLE 5

|  | Com. Ex. 4 | Com. Ex. 5 | Ex. 19 | Ex. 20 |
|---|---|---|---|---|
| Formulation (parts by mass) | | | | |
| SBR | 100 | 100 | 100 | 100 |
| Silica | 50 | 50 | 50 | 25 |
| Silane coupling agent | 2 | 2 | 2 | 2 |
| Reinforcing agent 5 | | | | 50 |
| Polymer E2 (modified) | | | 25 | |
| Polymer C2 (unmodified) | | 25 | | |
| Zinc white | 2 | 2 | 2 | 2 |
| Anti-aging agent | 2 | 2 | 2 | 2 |
| Stearic acid | 2 | 2 | 2 | 2 |
| Sulfur | 1.8 | 1.8 | 1.8 | 1.8 |
| Vulcanization accelerator | 1.8 | 1.8 | 1.8 | 1.8 |
| Secondary vulcanization accelerator | 1.5 | 1.5 | 1.5 | 1.5 |
| Physical properties | | | | |
| 25° C. dynamic elastic modulus E* (Mpa) | 7.9 | 13.5 | 17.8 | 21.5 |
| 25° C. tan δ | 0.19 | 0.20 | 0.20 | 0.19 |

Examples 21 and 22, and Comparative Example 7

Rubber compositions were prepared in the same manner as in Example 16 in the formulations (parts by mass) presented in Table 6, using a Banbury mixer. A test piece produced from each rubber composition was then used to determine 0° C. dynamic elastic modulus E* and tan δ, and 25° C. dynamic elastic modulus E* and tan δ. Measurements of 0° C. dynamic elastic modulus E* and tan δ were performed in the same manner as in the 25° C. dynamic elastic modulus E* and 25° C. tan δ measurements, except that the temperature was changed to 0° C.

The results are presented in Table 6. Comparative Example 7 with the unmodified polytridecyl methacrylate of the polymer C3 had an increased low-temperature tan δ value as compared to the control Comparative Example 4. Example 21 with the modified polytridecyl methacrylate of the polymer E3 had an even greater tan δ value. The tan δ value also increased in Example 22 in which the polymer grafted silica of the reinforcing agent 6 was contained. Because the polytridecyl methacrylate had a glass transition point in a low-temperature region, an increased low-temperature tan δ value was obtained while suppressing an increase of dynamic elastic modulus. The rubber compositions of Examples 21 and 22 are thus preferable in applications such as rubbers for high grip performance tires, and rubbers for winter tires.

TABLE 6

|  | Com. Ex. 4 | Com. Ex. 7 | Ex. 21 | Ex. 22 |
|---|---|---|---|---|
| Formulation (parts by mass) | | | | |
| SBR | 100 | 100 | 100 | 100 |
| Silica | 50 | 50 | 50 | 25 |
| Silane coupling agent | 2 | 2 | 2 | 2 |
| Reinforcing agent 6 | | | | 50 |
| Polymer E3 (modified) | | | 25 | |
| Polymer C3 (unmodified) | | 25 | | |
| Zinc white | 2 | 2 | 2 | 2 |
| Anti-aging agent | 2 | 2 | 2 | 2 |
| Stearic acid | 2 | 2 | 2 | 2 |
| Sulfur | 1.8 | 1.8 | 1.8 | 1.8 |
| Vulcanization accelerator | 1.8 | 1.8 | 1.8 | 1.8 |
| Secondary vulcanization accelerator | 1.5 | 1.5 | 1.5 | 1.5 |
| Physical properties | | | | |
| 0° C. dynamic elastic modulus E* (Mpa) | 9.4 | 7.9 | 8.5 | 8.5 |
| 0° C. tan δ | 0.24 | 0.31 | 0.35 | 0.36 |
| 25° C. dynamic elastic modulus E* (Mpa) | 7.9 | 6.8 | 7.5 | 7.2 |
| 25° C. tan δ | 0.19 | 0.20 | 0.19 | 0.19 |

As can be seen in Tables 4 to 6, the dynamic viscoelasticity varies according to the polymer added, and can be controlled by varying the type of the polymer.

As demonstrated by these results, the modified polymer with the introduced terminal alkoxysilyl group can be obtained by polymerizing a monomer with the silicon compound of the present embodiment used as a polymerization initiator, and the dynamic viscoelasticity of the rubber composition can be efficiently and desirably controlled by appropriately selecting the monomer. It was also demonstrated that the dynamic viscoelasticity of the rubber composition can be efficiently and desirably controlled by selecting the polymer (the monomer used) grafted to the reinforcing agent. The modified polymer or graft polymer may be a copolymer or a block copolymer of two or more monomers, and two or more kinds of modified polymers or reinforcing agents may be contained in the rubber component.

Evaluation of Plastic Composition

Example 23, and Comparative Examples 8 and 9

A pellet was formed by melt kneading the materials in the formulation (parts by mass) presented in Table 7, using a biaxial kneader (Research Laboratory of Plastics Technology Co., Ltd.). The pellet was T die molded into a film measuring 350 mm in width and 0.2 mm in thickness, using a single screw extruder. Details of the components shown in Table 7 are as follows.
Polyester: Toyobo Co., Ltd. "Pelprene P30B"
Silica: Tosoh Silica Corporation "Nipsil AQ"
Each film was measured for air permeability coefficient by using the following method.
Air Permeability Coefficient:
Air permeability coefficient was measured according to JIS K7126-1, using a gas permeability measurement device BT-3 available from Toyo Seiki Co., Ltd. (test gas: air; test temperature: 80° C.). The measurement result was represented as an index relative to the air permeability coefficient of the film of the Comparative Example 8 taken as 100. Smaller indices mean smaller air permeability coefficients, and superior gas barrier performance.

The results are presented in Table 7. Example 23 that contained the reinforcing agent 1 had a smaller air permeability coefficient than Comparative Example 9 in which silica and polymer C1 were mixed with polyester. This is due to the effect of the polymer grafted silica of reinforcing agent 1 being well dispersed in the polyester matrix and efficiently increasing the permeation path of the air molecules. On the other hand, the effect was limited in Comparative Example 9 in which silica was added alone, presumably because of the poorer dispersibility than in Example 23, though the effect of increasing the permeation path of the air molecules was observed. The plastic composition has use in applications such as containers, and wrapping materials.

TABLE 7

|  | Com. Ex. 8 | Com. Ex. 9 | Ex. 23 |
|---|---|---|---|
| Formulation (parts by mass) | | | |
| Polyester | 100 | 100 | 100 |
| Silica | | 50 | |
| Reinforcing agent 1 | | | 100 |
| Polymer C1 | | 50 | |
| Physical properties | | | |
| Air permeability (Index) | 100 | 90 | 60 |

INDUSTRIAL APPLICABILITY

The silicon compound according to the present embodiment can be used as, for example, a radical polymerization initiator, and to produce a polymer, and a solid substance-polymer graft chain complex such as a rubber or plastic reinforcing agent by taking advantage of the radical polymerization initiation capability.

The invention claimed is:

1. A silicon compound represented by the following general formula (1)

A-Z$^1$—S—Z$^2$—Si(OR$^1$)$_n$(R$^2$)$_{3-n}$     (1)

wherein A is represented by the general formula (2)

(2)

wherein R$^3$, R$^4$, and R$^5$ are each independently a hydrogen atom, a hydrocarbon group, or a halogen atom, and at least one selected from the group consisting of R$^3$, R$^4$, and R$^5$ is halogen, Z$^1$ and Z$^2$ are each independently a bivalent group that has at least a carbon atom, R$^1$ and R$^2$ are each independently an alkyl group having from 1 to 3 carbon atoms, and n is an integer of 1 to 3.

2. The silicon compound according to claim 1, wherein A is represented by the following formula (4-1), Z$^1$ is represented by the following formula (4-2), and Z$^2$ is represented by the following formula (4-3)

(4-1)

——(CH$_2$)$_a$——     (4-2)

——(CH$_2$)$_m$——     (4-3)

wherein X is halogen, R$^7$ and R$^8$ are each independently hydrogen, or an alkyl group having from 1 to 3 carbon atoms, and are not hydrogen at the same time, and wherein a is an integer of 3 to 11, and m is an integer of 1 to 3.

3. A method for producing a silicon compound represented by the following general formula (5), the method comprising reacting a compound represented by the following general formula (6) with a compound represented by the following general formula (7)

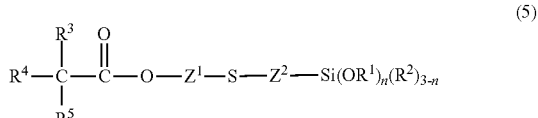

(5)

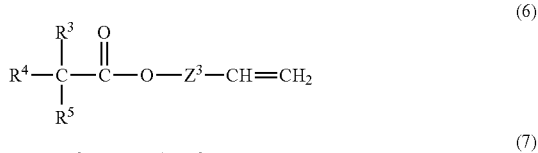

(6)

HS—Z$^2$—Si(OR$^1$)$_n$(R$^2$)$_{3-n}$     (7)

wherein R$^1$ and R$^2$ are each independently an alkyl group having from 1 to 3 carbon atoms, R$^3$, R$^4$, and R$^5$ are each independently a hydrogen atom, a hydrocarbon group or a halogen atom, and at least one selected from the group consisting of R$^3$, R$^4$, and R$^5$ is halogen, and wherein Z$^1$, Z$^2$, and Z$^3$ are each independently a bivalent group that has at least a carbon atom, and n is an integer of 1 to 3.

4. The method according to claim 3, wherein the compound represented by the general formula (6) is represented by the following general formula (8), the compound represented by the general formula (7) is represented by the following general formula (9), and the silicon compound represented by the general formula (5) is represented by the following general formula (4)

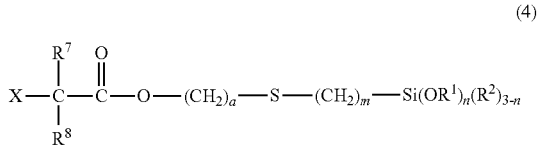

(4)

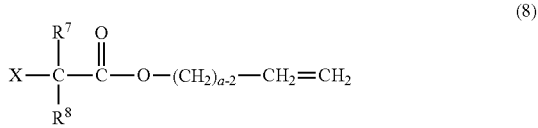

(8)

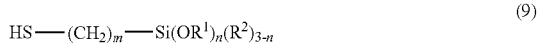

HS—(CH$_2$)$_m$—Si(OR$^1$)$_n$(R$^2$)$_{3-n}$     (9)

wherein X is halogen, R$^1$ and R$^2$ are each independently an alkyl group having from 1 to 3 carbon atoms, R$^7$ and R$^8$ are each independently hydrogen, or an alkyl group having from 1 to 3 carbon atoms, and are not hydrogen at the same time, and wherein a is an integer of 3 to 11, m is an integer of 1 to 3, and n is an integer of 1 to 3.

5. The method according to claim 3, wherein the compound represented by the general formula (6) and the compound represented by the general formula (7) are reacted with each other by using a radical generating agent as a reaction catalyst.

6. A radical polymerization initiator that comprises the silicon compound of claim 1.

7. A method for producing a polymer, the method comprising subjecting a monomer to radical polymerization or living radical polymerization with the radical polymerization initiator of claim 6.

8. A polymer having a terminal alkoxysilyl group and obtained by using the method of claim 7.

9. The polymer according to claim 8, wherein the polymer has a polymer chain resulting from living radical polymerization of the monomer, and a structure of the following formula (1-1) at one end of the polymer chain

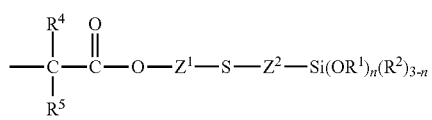

(1-1)

wherein $R^1$ and $R^2$ are each independently an alkyl group having from 1 to 3 carbon atoms, $R^4$ and $R^5$ are each independently a hydrogen atom, a hydrocarbon group, or a halogen atom, $Z^1$ and $Z^2$ are each independently a bivalent group that has at least a carbon atom, and n is an integer of 1 to 3.

10. A rubber composition comprising the polymer of claim 8 in 0.1 to 100 parts by mass with respect to 100 parts by mass of a rubber component.

11. A method for producing a complex, the method comprising fixing the silicon compound of claim 1 to a surface of a solid substance, and polymerizing a monomer from the fixed silicon compound through living radical polymerization to form a polymer graft chain.

12. The method for producing a complex according to claim 11, wherein the solid substance is at least one selected from the group consisting of a silica fine particle, a zinc oxide fine particle, a titanium oxide fine particle, and a barium titanate fine particle.

13. The method for producing a complex according to claim 11, wherein the monomer is at least one selected from the group consisting of a vinyl monomer and a diene monomer.

14. The method for producing a complex according to claim 11, wherein the amount of the polymer graft chain formed by living radical polymerization of the monomer is 5 to 1,000 parts by mass with respect to 100 parts by mass of the solid substance.

15. A complex obtained by using the method of claim 11.

16. A molded article that comprises the complex of claim 15.

17. A method for producing a rubber or plastic reinforcing agent, the method comprising fixing the silicon compound of claim 1 to a surface of a solid substance, and polymerizing a radically polymerizable monomer through living radical polymerization started from the fixed silicon compound at the group capable of initiating radical polymerization.

18. A rubber or plastic reinforcing agent obtained by using the method of claim 17, wherein the amount of the polymer graft chain on the solid substance surface is 5 to 1,000 parts by mass with respect to 100 parts by mass of the solid substance.

19. The rubber or plastic reinforcing agent according to claim 18, wherein the solid substance is at least one selected from the group consisting of a silica fine particle, a zinc oxide fine particle, a titanium oxide fine particle, and a barium titanate fine particle.

20. A rubber composition that comprises the reinforcing agent of claim 18 in 1 to 200 parts by mass with respect to 100 parts by mass of a rubber component.

21. A plastic composition that comprises the reinforcing agent of claim 18 in 1 to 200 parts by mass with respect to 100 parts by mass of a plastic component.

* * * * *